United States Patent [19]

Repka et al.

[11] Patent Number: 5,714,165
[45] Date of Patent: *Feb. 3, 1998

[54] BIOADHESIVE POLYETHYLENE GLYCOL OINTMENT FOR MEDICAMENTS

[75] Inventors: Michael A. Repka, Pleasanton; Thomas G. Gerding, Georgetown, both of Tex.

[73] Assignee: Mikkur, Inc., Pleasanton, Tex.

[*] Notice: The term of this patent shall not extend beyond the expiration date of Pat. No. 5,112,620.

[21] Appl. No.: 861,558

[22] Filed: Apr. 1, 1992

Related U.S. Application Data

[63] Continuation-in-part of Ser. No. 585,666, Sep. 20, 1990, Pat. No. 5,112,620.

[51] Int. Cl.⁶ .................... A61K 9/06; A61K 47/32; A61K 47/34; A61K 9/10
[52] U.S. Cl. .................. 424/486; 514/928; 514/969; 514/944
[58] Field of Search ............. 424/484, 486, 424/78.33; 514/180, 941, 929, 969, 626, 944

[56] References Cited

U.S. PATENT DOCUMENTS

| | | |
|---|---|---|
| Re. 33,093 | 10/1989 | Schiraldi et al. ............ 424/676 |
| 4,307,075 | 12/1981 | Martin ............ 428/28 |
| 4,627,977 | 12/1986 | Gaffar et al. ............ 424/52 |
| 4,764,378 | 8/1988 | Keith et al. ............ 424/435 |
| 4,765,983 | 8/1988 | Takayanagi et al. ............ 424/434 |
| 4,883,660 | 11/1989 | Blackman et al. ............ 424/78 |
| 4,910,247 | 3/1990 | Haldar et al. ............ 524/400 |
| 4,948,580 | 8/1990 | Browning ............ 424/78 |

FOREIGN PATENT DOCUMENTS 203613   8/1988   Japan.

OTHER PUBLICATIONS

"Topical Mucosal Adhesive Dosage Forms", T. Nagi, Medicinal Research Reviews, vol. 6, No. 2,227-242 (1986).

Primary Examiner—Edward J. Webman
Attorney, Agent, or Firm—W. R. Eberhardt

[57] ABSTRACT

A therapeutic composition having wet adherent properties and particularly useful for delivery of medicaments to mucosal surfaces comprises a therapeutically effective amount of a medicament dispersed in a base material comprising from about 3 to 15% by weight of a water soluble salt of a copolymer of methyl vinyl ether and maleic acid or anhydride and from about 85 to 97% by weight of polyethylene glycol. Formulations of the base material with triamcinolone acetonide and lidocaine are particularly efficacious in the treatment of recurrent aphthous ulcers.

33 Claims, No Drawings

BIOADHESIVE POLYETHYLENE GLYCOL OINTMENT FOR MEDICAMENTS

This is a continuation-in-part of application Ser. No. 07/589,666, filed Sep. 20, 1990, now U.S. Pat. No. 5,112,620.

FIELD OF THE INVENTION

The present invention relates to therapeutic compositions, and more particularly to bioadhesive compositions having wet adherent properties which are suitable for delivery of medicaments to mucosal surfaces and are particularly useful in the treatment of recurrent aphthous ulcers.

BACKGROUND OF INVENTION

Recurrent aphthous ulcers (RAU) or oral canker sores are the most common oral lesions afflicting humans. Studies have shown such ulcers affect 18% to 50% of the general population. As the name suggests, RAU lesions tend to recur in susceptible patients, often lasting for weeks. These lesions can be characterized as necrotizing ulcerations of oral mucosal tissue which are located on soft, non-keratinized mucosa. The lesions are painful, affect nutritional intake, and disrupt oral hygiene. They lead commonly to secondary infections by opportunistic organisms and sometimes result in scarring.

The etiology of RAU has been linked to several causative factors including allergies, trauma, stress, autoimmune dysfunction, nutritional deficiencies, microbial infection, hormonal changes, and systemic disease. However, several studies have shown that whatever the specific etiology in a particular patient, the clinical manifestations of RAU are due to an altered immune response. Immunosuppressive steroids such as triamcinolone acetonide have been found to be effective in the treatment of RAU. A problem with steroidal therapy for RAU however, is that administration in large doses or over extended periods can cause adrenal suppression and atrophy. The dosage necessary for steroidal therapy to have therapeutic effect for RAU can be lessened, thereby decreasing the opportunity and magnitude of harmful side effects, if the therapy is applied topically rather than systemically. Furthermore, treatment periods necessary to achieve the desired therapeutic effect can be shortened if the form of the product encourages patient compliance in applying the medication on a prescribed schedule.

Several methods of treatment for aphthous ulcers have been explored, including oral tape adhesives and bioadhesive compositions. For instance, U.S. Pat. Nos. 4,517,173 to Kizawa et al., 4,765,983 to Takawanagi et al., 4,772,470 to Inoue et al., and 4,876,092 to Mizobuchi et al. all disclose the use of oral tape adhesives. Through clinical experience, Applicants have discovered that oral mucosal tapes have very poor patient compliance. The tapes are awkward to apply, easily dislodged, and are a source of constant irritation and discomfort when applied to the oral mucosa.

Other attempts at delivery of medication to the oral mucosa have included bioadhesive compositions based primarily on organic cellulose, such as disclosed in Reissue Patent No. RE.33,093 issued to Schiraldi et al., and polycarbophils disclosed in U.S. Pat. No. 4,615,697 issued to Robinson. The major disadvantages of such compositions is that they are aqueous systems which do not provide as rapid symptomatic relief as the compositions of the present invention, and which are relatively easily removed from the oral mucosa by the flow of saliva.

U.S. Pat. No. 4,948,580 to Browning describes a bioadhesive composition comprising a freeze-dried polymer mixture formed of the copolymer poly(methyl vinyl ether/ maleic anhydride) and gelatin dispersed in an ointment base such as mineral oil containing dispersed polyethylene. The freeze-dried combination of polymer and gelatin is reported to be a synergistic combination having enhanced mucoadhesive properties compared to a simple mixture.

The present invention provides a novel and advantageous therapeutic composition by combining the therapeutic effect of steroids to counter the dysfunctional immune response associated with RAU, with a local anesthetic to provide immediate symptomatic relief, in an organic base material which provides optimal delivery of the active medications to the lesions. The base material of the present invention is a bioadhesive composition having wet adherent properties which is not readily displaced from the oral mucosa even in the presence of saliva, and which allows the active medications to remain concentrated and localized over the RAU lesions for an extended treatment period.

It is accordingly an object of the present invention to provide a therapeutic composition for effective local delivery of medicaments to mucosal surfaces. It is a further object of this invention to provide a therapeutic composition for the treatment of recurrent aphthous ulcers by the sustained local delivery of immunosuppressive agents. It is a further object of this invention to provide a composition for the topical treatment of RAU by efficiently delivering therapeutic levels of immunosuppressive agents to lesions by means of an ointment having wet adherent properties which is not easily removed from oral mucosa in the presence of saliva. A still further object of this invention is to provide a therapeutic composition which encourages patient compliance by providing rapid symptomatic relief to the pain of aphthous ulcers. A yet further object of this invention is to provide a novel bioadhesive composition useful in formulating therapeutic compositions having wet adherent properties. These and other objects, features and advantages of this invention will be apparent to those skilled in the art from the ensuing description and examples.

SUMMARY

The compositions of the present invention comprise a therapeutically effective amount of a medicament dissolved in a base material having wet adherent properties in contact with moist mucosal surfaces. The base material is a bioadhesive composition comprising from about 3 to 15% by weight of a water-soluble salt of a copolymer of methyl vinyl ether and maleic acid or anhydride and from about 85 to 97% by weight polyethylene glycol. The copolymer is preferably a mixed calcium and sodium salt having a molecular weight of between about 65,000 and 70,000. The polyethylene glycol preferably comprises a mixture of a low molecular weight material such as PEG 400 and a higher molecular weight material such as PEG 3350.

Therapeutic compositions of the present invention comprising a therapeutically effective amount of a medicament dispersed in the bioadhesive base material are particularly useful in the treatment of recurrent aphthous ulcers wherein the medicament is an immunosuppressive steroid such as triamcinolone acetonide which is soluble in the PEG component of the base material. The therapeutic composition may also include a topical anesthetic such as lidocaine to provide immediate symptomatic relief to the patient. When applied to an aphthous ulcer on the oral mucosa, the therapeutic composition adheres to the mucosal surface and delivers the medicament to the area of application over an extended period of time, thereby accelerating the healing rate of the ulcer.

DETAILED DESCRIPTION

The therapeutic compositions of the present invention comprise a novel base material having wet adherent properties and a therapeutically effective amount of one or more medicaments incorporated in said base material. The base material is a bioadhesive composition comprising from about 3 to 15% by weight of a water soluble salt of a copolymer of a lower alkyl vinyl ether and maleic acid or maleic anhydride in polyethylene glycol (PEG). The PEG preferably comprises a mixture of a low molecular weight PEG which is a liquid at 30° C. and a high molecular weight PEG which is a waxy solid at 30° C. in proportions which result in the mixture having an ointment like consistency at room temperature. Suitable mixtures comprise from about 40 to 60% PEG having a molecular weight of less than 600, most preferably PEG 400, admixed with about 20 to 50% PEG having a molecular weight above 600, most preferably PEG 3350. The PEG component of the bioadhesive composition may conform to that described for ointments in the official monograph of the U.S. Pharmacopoeia (1990) at page 1963.

The alkyl vinyl ether/maleic acid or anhydride copolymers suitable for use in the base material are described in U.S. Pat. No. 4,910,247, incorporated herein by reference. In general, these copolymers have from about 40 to about 90%, preferably from about 70 to 90%, of the initial carboxyl groups reacted with a metal, and have a molecular weight of between about 18,000 and about 80,000, preferably between about 40,000 and about 60,000 as measured by membrane osmometry in 2-butanone (1–10 grams/1000 ml solution). The various metal salts of the copolymer can be prepared by reacting the desired amount of metal hydroxide with a lower alkyl vinyl ether/maleic acid or maleic anhydride copolymer having a molecular weight of from about 18,000 to about 80,000. Such alkyl vinyl ether/maleic acid or anhydride copolymers are commercially available from GAF Corporation and sold as GANTREZ™ S series (MW approximately equal to 18,000–70,000; MS series (MW approximately equal to 60,000–75,000) and AN series (MW approximately equal to 18,000–80,000). The resultant metal salt product in which a portion of the original carboxyl groups are neutralized, is then dried and milled to a Suitable particle size.

For purposes of the present invention, the copolymer is preferably a blend comprising a divalent calcium salt and a monovalent sodium salt of a methyl vinyl ether/maleic acid copolymer wherein the concentration of Ca is between about 10 and 15 wt. % of the blend; the concentration of Na is between about 1.5 and about 4 wt. % of the blend, and free acid-COOH represents between about 9 and about 25 wt. % of the blend. Alternatively, a commercially available calcium and sodium salt mixture of a methyl vinyl ether/maleic acid copolymer can be used in the present mixture. Such a polymeric salt blend is supplied by GAF Corporation as GANTREZ™ MS-955 wherein the concentration of Ca is between about 11 and 13 wt. % of the blend, the concentration of Na is between about 2 and 2.5 wt. % of the blend, the proportion of Ca:Na is about 5–6:1 and the molecular weight is about 65,000–70,000.

The medicament incorporated in the therapeutic compositions of the present invention may be any therapeutically active agent or combination of agents useful in the topical treatment of wounds, rashes, ulcers and other conditions. The medicaments are preferably soluble in at least the low molecular weight PEG component of the base material, since dissolved medicaments are generally found to have greater availability and provide faster relief than those which are insoluble and merely dispersed in the base material. Nevertheless, insoluble dispersed medicaments may be suitable or even preferred for certain treatment applications. While the compositions of the present invention are particularly useful in the treatment of aphthous ulcers, the utility of the compositions is not so limited. The compositions of the present invention may also be used in the topical application of medicaments to other mucous membranes in nasal, rectal and vaginal applications as well as oral applications. In addition, the compositions of the present invention may be used in the general treatment of wounds, abrasions and other epidermal conditions where topical medicaments commonly find application.

By way of illustration, medicaments which may be employed in the therapeutic compositions of the present invention include antifungal agents such as amphotericin B, nystatin, griseofulvin, miconazole, ketoconazole, econazole, clotrimazole, and other macrolide antifungal agents; antibacterials such as metronidazole, penicillins, monobactams, ampicillin, neomycin, erythromycin, mupirocin, tyrothricin, gramicidin, cephalosporins, gentamycin and other aminoglycosides; antihistamines such as chlorpheniramine, diphenhydramine, promethazine, phenylpropanolamine, brompheniramine, doxylamine, tripelennamine, pyrilamine, and triprolidine; anti-cancer agents such as 5-fluorouracil; anti-inflammatory agents such as hydrocortisone; other known steroids such as prednisone, prednisolone, triamcinolone, dexamethasone, betamethasone and fluocinonide/fluocinolone acetonide; hemostatic agents such as epinephrine, aluminum chloride, ferric chloride, thrombin, collagen, carboxymethylcellulose and oxidized cellulose; hormones such as oestriol; analgesic and anti-inflammatory agents such as acetaminophen, phenacetin, aspirin, aminopyrine, sulpyrine, phenylbutazone, mefenamic acid, flufenamic acid, ibufenac, ibuprofen, indomethacin, colchicine, and probenecid; and anti-viral agents such as acyclovir, ribavarin, trifluorothyridine or idoxuridine; antiseptics such as hexachlorophene, tetramethyl thiuramdisulfide, benzalkonium chloride, cetylpyridium chloride, eugenol, thimerosal, hexylresorcinol, cresols, zinc oxide, methylene blue, boric acid, chloramine-T, gentian violet, phenyl mercuric chloride, phenyl mercuric nitrate basic, acriflavine, sodium perborate, metallic peroxides such as sodium peroxide, sodium permanganate, and the halogens. The medicament may be present in an amount within the range of from about 0.01 to about 25% and preferably from about 0.05 to about 15% by weight depending upon the particular medicament employed and the desired site of action.

For the treatment of aphthous ulcers, the medicament is preferably an immunosuppressive steroid such as triamcinolone acetonide which is known to be effective for this purpose. In addition, the therapeutic composition also preferably includes a topical anesthetic such as lidocaine, benzocaine, bupivacaine, cocaine, dyclonine, mepivacaine, procaine, prilocaine, propoxycaine, chloroprocaine, tetracaine or their hydrochloride salts to provide rapid symptomatic relief to the patient. In a preferred formulation for the treatment of aphthous ulcers, the base material comprises a mixture of from about 3 to 15% by weight GANTREZ MS-955, from 40 to 60% by weight PEG 400 and 20 to 50% by weight PEG 3350. The active components of the composition comprise from about 0.01 to 0.03%, most preferably from about 0.09 to 0.15 by weight triamcinolone acetonide, and from about 0.25 to 5%, most preferably from about 1.5 to 2.5% by weight lidocaine, both of which are soluble in PEG 400. Such compositions, when applied to an aphthous ulcer in the oral cavity, are found to adhere well to the mucosal surface and to dissolve slowly in the saliva whereby the medicament is delivered and the treatment maintained for a period of 15 minutes or longer. In comparison therewith, compositions based only on the PEG ointment without the copolymer component do not adhere well to the applied surface and dissolve more rapidly in the saliva, whereby the treatment is effective for a period of only a few minutes.

In addition to the active medicaments and anesthetic, the therapeutic compositions of the present invention may contain other components to modify the physical or esthetic properties thereof, such as coloring agents, flavoring agents, viscosity modifiers, gelling agents, antioxidants, preservatives and the like. Conventional preservatives such as methyl paraben and propyl paraben and antioxidants such as butylated hydroxytolulene and butylated hydroxyanisole are desirably included to prevent bacterial contamination and increase storage stability.

The present invention is illustrated by the following examples directed to the treatment of recurrent aphthous ulcers. For these examples, a series of therapeutic adhesive compositions were prepared to the formulations set forth below. All parts and percentages are by weight unless otherwise specified.

| Formulation | Base Material | | |
|---|---|---|---|
| | GANTREZ MS-955 | PEG 400 | PEG 3350 |
| A | 2.4% | 47.6% | 47.6% |
| B | 4.9 | 51.0 | 41.9 |
| C | 5.5 | 52.2 | 40.0 |
| D | 6.0 | 52.2 | 39.5 |
| E | 6.5 | 52.2 | 39.0 |
| F | 7.0 | 52.2 | 38.5 |
| G | 7.5 | 52.2 | 38.0 |
| H | 8.0 | 52.2 | 37.5 |
| I | 10.0 | 52.5 | 35.5 |

All formulations contained the following active components:

2.0% lidocaine 0.1% Triamcinolone acetonide 0.18% methyl paraben-preservative 0.02% propyl paraben-preservative 0.05% butylated hydroxtoluene (BHT)—antioxidant Therapeutic compositions were prepared for patent evaluation by adding the BHT to the PEG-400 with heating as necessary to dissolve the BHT. The solution was allowed to cool to approximately 50° C. and the other components added in the following order: GANTREZ, remaining active components, PEG-3350. The mixture was stirred until a uniform consistency was obtained and allowed to cool to room temperature. The resulting composition was an ointment which was readily dispensed from a collapsible tube.

The efficacy of the various formulations of the present invention was determined in a series of clinical studies wherein the formulations were evaluated subjectively for pain relief, healing rate and ease of application by patients afflicted with recurrent aphthous ulcers. In these examples, pain was rated 0–5 with 5 being the most severe, healing rate was rated 0–5 with 5 indicating the most rapid rate, and duration of pain was measured as number of days during which the patient experienced significant discomfort.

On the basis of the clinical studies, it was determined that the GANTREZ MS-955 copolymer component is most preferably present in an amount of from about 4.5 to 7% by weight of the composition. At lower concentrations, the wet adherent properties of the composition are diminished, while at higher concentrations the copolymer forms a grainy suspension in the PEG which tends to make the product more difficult to apply and diminishes patient compliance and acceptance.

EXAMPLE 1

A clinical trial was conducted with eight patients who contracted aphthous ulcers at least four times per year. All patients had active episodes of aphthous ulcers at the time of the trials. Four subjects were given Formulation B of the present invention. The other four subjects were given a commercially available benzocaine ointment containing 20% benzocaine in a denture adhesive-like base as the control. In a subsequent ulcer episode, all eight patients were crossed over so that all patients used both products. Average patient response in this clinical study is reported in Table I below:

TABLE I

| Treatment | Average Patient Response | | |
|---|---|---|---|
| | Initial Pain | 30 min. Pain | Healing Rate |
| Control | 4.25 | 2.25 | 3 |
| Formulation B | 4.75 | 1.0 | 4.25 |
| Control | 4.25 | 1.75 | 3.5 |
| Formulation B | 4.5 | 0.75 | 4.5 |

The above data demonstrate a significant improvement in both initial pain relief and healing rate for the formulation of this invention as compared to the commercial benzocaine ointment.

EXAMPLE 2

Clinical trials were performed on 20 patients afflicted with aphthous ulcers in a single blind crossover study comparing Formulation C of the present invention with a placebo consisting of the same base material having no active components. Ulcers treated were located throughout the mouth on the tongue, cheeks, lips and gums. The average patient response was as shown in Table II below:

TABLE II

| Treatment | Average Patient Response | | |
|---|---|---|---|
| | Initial Pain | 20 min. Pain | Duration of Pain |
| Placebo | 4 | 3.5 | 3.8(1.5–5.5) |
| Formulation C | 4.2 | 0.8 | 1.5(0.5–2.5) |

The above data demonstrate that, as expected, no significant pain relief was experienced with the placebo treatment, while excellent relief was provided by Formula C even 20 minutes after treatment. The average duration of pain with the Formulation C treatment was furthermore reduced to less than half of that experienced with the placebo indicating a very good healing rate. The range on duration of pain is given in parentheses.

EXAMPLE 3

A clinical trial was conducted with 16 patients to compare Formulation E of the present invention with a commercially available liquid formulation comprising an aqueous solution of CuSO$_4$, iodine, potassium iodide and alcohol. Healing time was observed to be shorter for 12 of the patients treated with Formulation E and equivalent in the other four patients. Greater pain relief with Formulation E was reported by 15 of the 16 patients 20 minutes after treatment. Average patient response is summarized in Table III below:

TABLE III

| Treatment | Average Patient Response | | |
|---|---|---|---|
| | Initial Pain | 20 min. Pain | Duration of Pain |
| Control | 4.1 | 1.75 | 2.8(1.5–4.0) |
| Formulation E | 4.1 | 0.75 | 1.7(0.5–3.5) |

In addition to the improved clinical response experienced by patients with Formulation E, 15 of the 16 patients also expressed a preference for Formulation E in terms of convenience of use.

EXAMPLE 4

A clinical trial was conducted with 12 patients to compare Formulation F of the present invention with a commercial treatment product comprising 0.1% triamcinolone acetonide in an ointment base comprising a mixture of pectin, gelatin, carboxy methyl cellulose sodium, polyethylene glycol and mineral oil. As in Example 3, the composition of the present invention provided superior pain relief and increased healing rate in most cases and was preferred for use by all 12 patients. Average patient response is summarized in Table IV below:

TABLE IV

| Treatment | Average Patient Response | | |
|---|---|---|---|
| | Initial Pain | 20 min. Pain | Duration of Pain |
| Control | 4.1 | 2.7 | 2.5(1.5–3.5) |
| Formulation F | 4.0 | 0.8 | 1.5(0.5–2.5) |

As demonstrated by the above examples, the present invention provides a composition for the treatment of recurrent aphthous ulcers which efficiently delivers immunosuppressive agents to the lesions by topical application to the oral mucosa, and which encourages patient compliance by providing rapid symptomatic relief which endures for at least 20 to 30 minutes. Although the invention has been described in conjunction with the foregoing specific embodiments, many alternatives, variations and modifications will be apparent to those of ordinary skill in the art and are included within the spirit and scope of the present invention. Moreover, while the preceding examples have been directed to therapeutic compositions specifically formulated for the treatment of recurrent aphthous ulcers, it will be appreciated that the medicament delivery characteristics afforded by the base material of these formulations can be utilized in other wound treatment applications, particularly in conjunction with the application of medicaments to mucous membrane surfaces where body fluids have a tendency to wash the medicament from the site of treatment. All such applications and methods of treatment are contemplated by and included in the present invention.

What is claimed is:

1. A therapeutic composition having wet adherent properties comprising a base material and a therapeutically effective amount of medicament incorporated therein, said base material comprising from about 3 to 15% by weight of a water soluble salt of a copolymer of a lower alkyl vinyl ether and maleic acid or anhydride and from about 85 to 97% by weight of polyethylene glycol (PEG).

2. The composition of claim 1 wherein said copolymer is a sodium salt, a calcium salt, or a mixture thereof.

3. The composition of claim 2 wherein said copolymer comprises a blend of a divalent calcium salt and monovalent sodium salt wherein the concentration of calcium is between about 10 and 15% by weight, the concentration of sodium is between about 1.5 and 4% by weight, and the free acid is between about 9 and 25% by weight.

4. The composition of claim 3 wherein the copolymer is methyl vinyl ether/maleic acid and concentration of calcium is between about 11 and 13% by weight, the concentration of sodium is between about 2 and 2.5% by weight, the ratio of Ca:Na is about 5–6:1, and the molecular weight of the copolymer is about 65,000–70,000.

5. The composition of claim 1 wherein said polyethylene glycol comprises a mixture of a first polyethylene glycol which is a liquid at 30° C. and a second polyethylene glycol which is a waxy solid at 30° C.

6. The composition of claim 5 wherein said first polyethylene gycol has a molecular weight of less than 600 and said second polyethylene glycol has a molecular weight greater than 600.

7. The composition of claim 6 comprising from about 40 to 60% by weight PEG 400 and from about 20 to 50% by weight PEG 3350.

8. The composition of claim 1 wherein said medicament comprises an anesthetic and asteroid.

9. The composition of claim 8 wherein said anesthetic is lidocaine or benzocaine.

10. The composition of claim 8 wherein said steroid is triamcinolone acetonide.

11. The composition of claim 1 wherein said medicament comprises from about 0.25 to 5.0% lidocaine and from about 0.01 to 0.3% triamcinolone acetonide by weight of said composition.

12. A composition for the topical treatment of recurrent aphthous ulcers comprising a therapeutically effective amount of medicament comprising an anesthetic and asteroid effective in the treatment of said ulcers dispersed in from about 3 to 15% by weight of a water soluble salt of a copolymer of methyl vinyl ether and maleic acid or anhydride, and from about 85 to 97% by weight of polyethylene glycol.

13. The composition of claim 12 wherein said steroid is triamcinolone acetonide.

14. The composition of claim 13 wherein said triamcinolone acetonide is present at a concentration of from about 0.01 to 0.3% by weight of said composition.

15. The composition of claim 14 wherein said anesthetic is lidocaine present at a concentration of from about 0.25 to 5% by weight of said composition.

16. The composition of claim 15 wherein the concentration of said triamcinolone acetonide is from about 0.09 to 0.15% and the concentration of said lidocaine is from about 1.5 to 2.5% by weight.

17. The composition of claim 12 wherein said copolymer comprises from about 4.5 to 7.0% by weight said composition.

18. The composition of claim 12 wherein said copolymer is a sodium salt, a calcium salt, or a mixture thereof.

19. The composition of claim 18 wherein said copolymer comprises a blend of the divalent calcium salt and monovalent sodium salt wherein the concentration of calcium is between about 10 and 15% by weight, the concentration of sodium is between about 1.5 and 4% by weight, and the free acid is between about 9 and 25% by weight.

20. The composition of claim 19 wherein the concentration of calcium is between about 11 and 13% by weight, the concentration of sodium is between about 2 and 2.5% by weight, the ratio of Ca:Na is about 5–6:1, and the molecular weight of the copolymer is about 65,000–70,000.

21. The composition of claim 12 wherein said polyethylene glycol comprises a mixture of a first polyethylene glycol which is a liquid at 30° C. and a second polyethylene glycol which is a waxy solid at 30° C.

22. The composition of claim 21 wherein said first polyethylene glycol has a molecular weight of less than 600 and said second polyethylene glycol has a molecular weight greater than 600.

23. The composition of claim 22 comprising from about 40 to 60% PEG 400 and from about 20 to 50% PEG 3350.

24. A method for the treatment of recurrent aphthous ulcers which comprises topically applying to said ulcers the composition of claim 12.

25. A method for the treatment of recurrent aphthous ulcers which comprises topically applying to said ulcers the composition of claim 16.

26. A method for the treatment of recurrent aphthous ulcers which comprises topically applying to said ulcers the composition of claim 20.

27. A bioadhesive composition comprising from about 3 to 15% by weight of a water-soluble salt of a copolymer of a lower alkyl vinyl ether and maleic acid or anhydride and from about 85 to 97% by weight of polyethylene glycol (PEG).

28. The composition of claim 27 wherein said copolymer is a sodium salt, a calcium salt, or a mixture thereof.

29. The composition of claim 28 wherein said copolymer comprises a blend of a divalent calcium salt and monovalent sodium salt wherein the concentration of calcium is between about 10 and 15% by weight, the concentration of sodium is between about 1.5 and 4% by weight, and the free acid is between about 9 and 25% by weight.

30. The composition of claim 29 wherein the copolymer is methyl vinyl ether/maleic acid and concentration of calcium is between about 11 and 13% by weight, the concentration of sodium is between about 2 and 2.5% by weight, the ratio of Ca:Na is about 5–6:1, and the molecular weight of the copolymer is about 65,000–70,000.

31. The composition of claim 27 wherein said polyethylene glycol comprises a mixture of a first polyethylene glycol which is a liquid at 30° C. and a second polyethylene glycol which is a waxy solid at 30° C.

32. The composition of claim 31 wherein said first polyethylene glycol has a molecular weight of less than 600 and said second polyethylene glycol has a molecular weight greater than 600.

33. The composition of claim 32 comprising from about 40 to 60% by weight PEG 400 and from about 20 to 50% by weight PEG 3350.

* * * * *